(12) United States Patent
Tsukada et al.

(10) Patent No.: US 10,737,927 B2
(45) Date of Patent: Aug. 11, 2020

(54) LIQUID SUPPLY APPARATUS

(71) Applicants: TSUKADA MEDICAL RESEARCH CO., LTD., Shinjuku-ku, Tokyo (JP); JAPAN AEROSPACE EXPLORATION AGENCY, Chofu-shi, Tokyo (JP); MITSUBISHI HEAVY INDUSTRIES, LTD., Minato-ku, Tokyo (JP)

(72) Inventors: Osamu Tsukada, Nagano (JP); Akihiko Nakasa, Nagano (JP); Kengo Kanai, Nagano (JP); Masato Shimizu, Nagano (JP); Haruna Koike, Nagano (JP); Nami Hatakeyama, Nagano (JP); Naoki Takizawa, Nagano (JP); Masaki Shirakawa, Ibaraki (JP); Hiroyasu Mizuno, Ibaraki (JP); Atsuko Homma, Ibaraki (JP); Dai Shiba, Ibaraki (JP); Akane Yumoto, Ibaraki (JP); Hirochika Murase, Tokyo (JP); Makoto Ohira, Tokyo (JP)

(73) Assignees: TSUKADA MEDICAL RESEARCH CO., LTD., Shinjuku-ku, Tokyo (JP); JAPAN AEROSPACE EXPLORATION AGENCY, Chofu-shi, Tokyo (JP); MITSUBISHI HEAVY INDUSTRIES, LTD., Minato-ku, Tokyo (JP)

( * ) Notice: Subject to any disclaimer, the term of this patent is extended or adjusted under 35 U.S.C. 154(b) by 383 days.

(21) Appl. No.: 15/525,546

(22) PCT Filed: Nov. 10, 2015

(86) PCT No.: PCT/JP2015/081529
§ 371 (c)(1),
(2) Date: May 9, 2017

(87) PCT Pub. No.: WO2016/076281
PCT Pub. Date: May 19, 2016

(65) Prior Publication Data
US 2017/0318780 A1 Nov. 9, 2017

(30) Foreign Application Priority Data

Nov. 10, 2014 (JP) .................................. 2014-227891

(51) Int. Cl.
*B67D 1/08* (2006.01)
*A01K 7/02* (2006.01)
(Continued)

(52) U.S. Cl.
CPC ............ *B67D 1/0894* (2013.01); *A01K 7/022* (2013.01); *B67D 3/042* (2013.01); *A61M 5/152* (2013.01); *B65D 83/0061* (2013.01)

(58) Field of Classification Search
CPC ....... B67D 3/042; A01K 7/022; A01K 5/0275
See application file for complete search history.

(56) References Cited

U.S. PATENT DOCUMENTS 2,011,884 A * 8/1935 Watkins ............... B67D 1/0412
141/18
3,089,463 A * 5/1963 Grunzke .................. A01K 7/02
119/71
(Continued)

FOREIGN PATENT DOCUMENTS

JP S61-81953 A 4/1986
JP 2002-017191 A 1/2002
(Continued)

OTHER PUBLICATIONS

"Polyisoprene Rubber," Ashby et al. Engineering Materials 2 (Fourth Edition) (Year: 2013).*
(Continued)

*Primary Examiner* — Magdalena Topolski
*Assistant Examiner* — Morgan T Barlow
(74) *Attorney, Agent, or Firm* — Harness, Dickey & Pierce, P.L.C.

(57) ABSTRACT

There is provided a liquid supply apparatus eliminating the need for a power supply, having relatively light weight and small footprint, and ensuring a stable liquid supply. The
(Continued)

liquid supply apparatus includes a first support member, a second support member, a balloon having one end supported by the first support member and the other end supported by the second support member, and a casing having a constant longitudinal length. The balloon is disposed in the casing and is configured so as to be able to hold a liquid therein and discharge the liquid therefrom. When the balloon holds the liquid, the one end and the other end of the balloon are positioned in the case.

10 Claims, 6 Drawing Sheets

(51) Int. Cl.
*B67D 3/04* (2006.01)
*A61M 5/152* (2006.01)
*B65D 83/00* (2006.01)

(56) References Cited

U.S. PATENT DOCUMENTS

| | | | | |
|---|---|---|---|---|
| 3,192,915 | A * | 7/1965 | Norris | A01K 5/0275 124/77 |
| 3,309,843 | A * | 3/1967 | Rigopulos | H01M 8/06 95/117 |
| 3,442,486 | A * | 5/1969 | Serio, Jr. | B67D 1/0418 251/155 |
| 3,486,539 | A * | 12/1969 | Candido | A61M 5/00 141/329 |
| 3,696,969 | A * | 10/1972 | De Van | B65D 77/067 222/105 |
| 3,993,069 | A | 11/1976 | Buckles et al. | |
| 4,386,929 | A * | 6/1983 | Peery | A61M 5/152 222/211 |
| 4,419,096 | A | 12/1983 | Leeper et al. | |
| 4,458,830 | A * | 7/1984 | Werding | B65D 83/0055 222/131 |
| 4,483,465 | A * | 11/1984 | Lawrence | B67D 3/042 222/502 |
| 4,658,990 | A * | 4/1987 | Ramage | A47G 21/18 141/18 |
| 4,834,801 | A * | 5/1989 | Kalla | A01K 1/0356 119/417 |
| 4,927,061 | A * | 5/1990 | Leigh | B67D 3/042 137/801 |
| 5,137,175 | A | 8/1992 | Kowalski et al. | |
| 5,284,481 | A * | 2/1994 | Soika | A61M 5/152 206/370 |
| 5,497,911 | A * | 3/1996 | Ellion | B05B 11/0059 222/95 |
| 5,542,584 | A * | 8/1996 | Konar | B65D 47/2025 222/505 |
| 5,622,282 | A * | 4/1997 | Yazawa | B65D 83/38 222/105 |
| 5,897,530 | A * | 4/1999 | Jackson | A61M 5/152 604/132 |
| 5,915,595 | A * | 6/1999 | Dow | B65D 83/62 222/105 |
| 7,021,495 | B2 * | 4/2006 | De Laforcade | B05B 11/0059 222/105 |
| 7,753,884 | B2 * | 7/2010 | Gallnbock | A61M 5/1483 222/105 |
| 9,968,038 | B2 * | 5/2018 | Alassadi | A01G 27/003 |
| 2005/0178798 | A1 | 8/2005 | Canegallo | |
| 2010/0239708 | A1 * | 9/2010 | Bachman | A01K 5/00 426/2 |
| 2013/0119092 | A1 | 5/2013 | Kuwagaki et al. | |
| 2013/0292412 | A1 * | 11/2013 | Jones | B67D 3/042 222/81 |
| 2013/0306676 | A1 * | 11/2013 | Fishel | B65D 77/067 222/105 |
| 2018/0050359 | A1 * | 2/2018 | Chang | A45D 34/00 |
| 2018/0111816 | A1 * | 4/2018 | Stever | B67D 3/043 |
| 2018/0282052 | A1 * | 10/2018 | Har-Shai | B65D 83/0061 |
| 2018/0305197 | A1 * | 10/2018 | Aiello | B67D 3/0067 |
| 2019/0030809 | A1 * | 1/2019 | Gasso | B65D 7/06 |
| 2019/0159572 | A1 * | 5/2019 | Tarajano | A45D 40/28 |

FOREIGN PATENT DOCUMENTS

| | | |
|---|---|---|
| JP | 2005-523210 A | 8/2005 |
| JP | 2006-311921 A | 11/2006 |
| WO | WO-2012-011558 A1 | 1/2012 |

OTHER PUBLICATIONS

International Search Report and Written Opinion of the International Searching Authority issued in PCT/JP2015/081529, dated Feb. 9, 2016; ISA/JP.

Extended European Search Report in corresponding EP Application No. 15859124.8 dated Jun. 7, 2018.

Office Action dated Oct. 18, 2019 in corresponding European Patent Application No. 15859124.8.

* cited by examiner

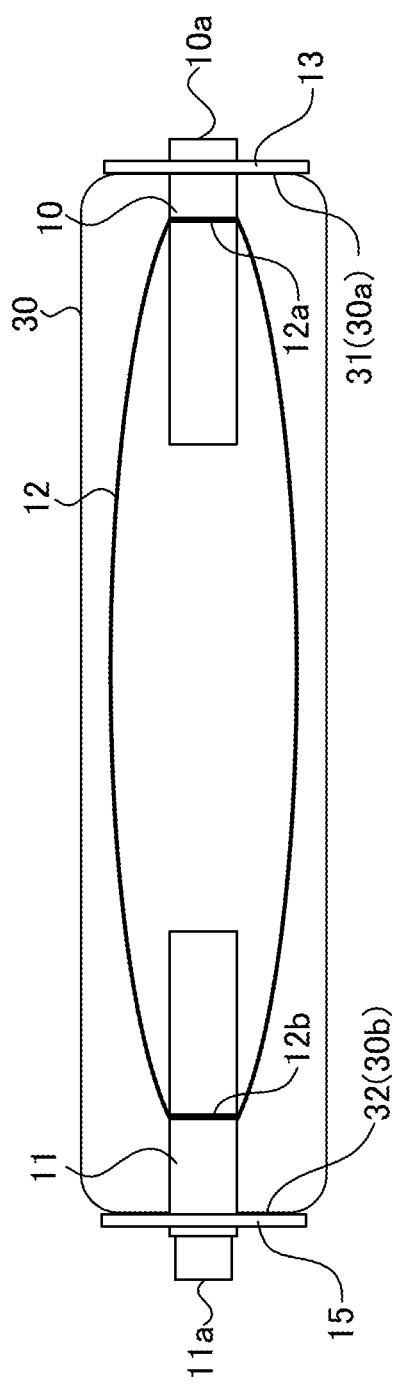

LIQUID SUPPLY APPARATUS

CROSS REFERENCE TO RELATED APPLICATIONS

This application is a U.S. National Phase Application under 35 U.S.C. 371 of International Application No. PCT/JP2015/081529 filed on Nov. 10, 2015 and published in Japanese as WO 2016/076281 A1 on May 19, 2016, which is based on and claims the benefit of priority from Japanese Patent Application No. 2014-227891 filed on Nov. 10, 2014. The entire disclosures of all of the above applications are incorporated herein by reference.

TECHNICAL FIELD

The present invention relates to a liquid supply apparatus and more particularly to a liquid supply apparatus for supplying a liquid for rearing organisms such as mice.

BACKGROUND ART

Recent years have seen experiments conducted for the purpose of studying the effects of a zero gravity environment or a microgravity environment on organisms in outer space so as to rear organisms such as mice flown on a spacecraft such as space shuttle in outer space. The rearing environment for mice or the like in outer space requires facilities for supplying mice or the like with water or liquid diet (hereinafter referred to as water or the like) in the same manner as in the case of rearing mice or the like on the ground. Examples of common facilities for supplying water or the like to mice or the like on the ground include an automatic liquid supply apparatus using gravity. However, such an automatic liquid supply apparatus using gravity cannot be used in a zero gravity environment.

In light of this, examples of facilities for supplying water or the like to mice or the like in outer space may be considered to include a device for automatically supplying water or the like using a motor-driven syringe pump or the like. However, such a motor-driven device needs a power supply and has a relatively heavy weight and large footprint. Therefore, it is not preferable to install such a motor-driven device in a spacecraft with limited loading weight and loading space. In addition, motor-driven devices may fail. A failure of the motor-driven device requires a repair by an astronaut and involves a time-consuming maintenance and management effort.

CITATION LIST

Patent Literature

Patent Literature 1: Japanese Patent Laid-Open No. 2002-017191

SUMMARY OF INVENTION

Technical Problem

In view of the problems of the prior art described above, the present invention has been made, and an object of the present invention is to provide a liquid supply apparatus eliminating the need for a power supply, having relatively light weight and small footprint, and ensuring a stable liquid supply.

Solution to Problem

A liquid supply apparatus according to an embodiment of the present invention includes a first support member; a second support member; a balloon having one end supported by the first support member and another end supported by the second support member; and a casing having a constant longitudinal length. The balloon is disposed in the casing and is configured so as to be able to hold therein a liquid to be supplied and discharge the held liquid. When the balloon holds the liquid, the one end and the other end of the balloon are positioned in the case.

In the liquid supply apparatus according to another embodiment of the present invention, the first support member is fixed to one end of the casing, the second support member is fixed to another end of the casing, and the balloon is supported by the first support member and the second support member in a state where a tensile stress is applied.

In the liquid supply apparatus according to yet another embodiment of the present invention, the balloon is supported by the first support member and the second support member in a state where a tensile stress is applied so as to have a length of 1.5 times or more in an axial direction of the first support member than that in a state where no tensile stress is applied.

In the liquid supply apparatus according to yet another embodiment of the present invention, the first support member is fixed to one end of the casing, and when the balloon holds the liquid, an axial expansion coefficient of the first support member of the balloon is greater than a radial expansion coefficient of the first support member of the balloon.

In the liquid supply apparatus according to yet another embodiment of the present invention, the first support member includes an outlet port for letting out the liquid held in the balloon; the second support member includes a filling port for filling the liquid into the balloon; and the balloon includes an outlet hole in fluid communication with the outlet port of the first support member and a filling hole in fluid communication with the filling port of the second support member.

In the liquid supply apparatus according to yet another embodiment of the present invention, the balloon is made of silicone rubber.

In the liquid supply apparatus according to yet another embodiment of the present invention, the liquid is a liquid for rearing organisms.

In the liquid supply apparatus according to yet another embodiment of the present invention, the liquid supply apparatus is used in outer space.

Advantageous Effects of Invention

The present invention can provide a liquid supply apparatus eliminating the need for a power supply, having relatively light weight and small footprint, and ensuring a stable liquid supply.

BRIEF DESCRIPTION OF DRAWINGS

FIG. 2C is a schematic side view of the liquid supply apparatus according to the second embodiment of the present invention.

DESCRIPTION OF EMBODIMENTS

Figure 1A:
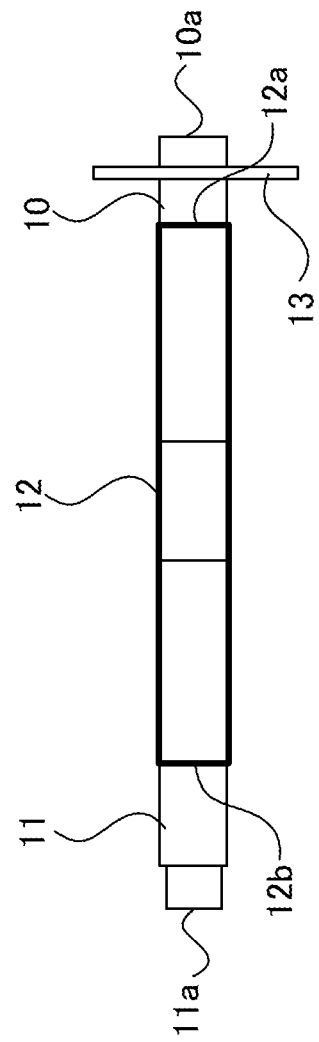
FIG. 1A is a schematic side view of a liquid supply apparatus according to a first embodiment of the present invention.

Hereinafter, the embodiments of the present invention will be described with reference to the drawings. In the drawings described below, the same reference numerals or characters are assigned to the same or similar components, and the duplicate description is omitted.

First Embodiment

Figure 1B:
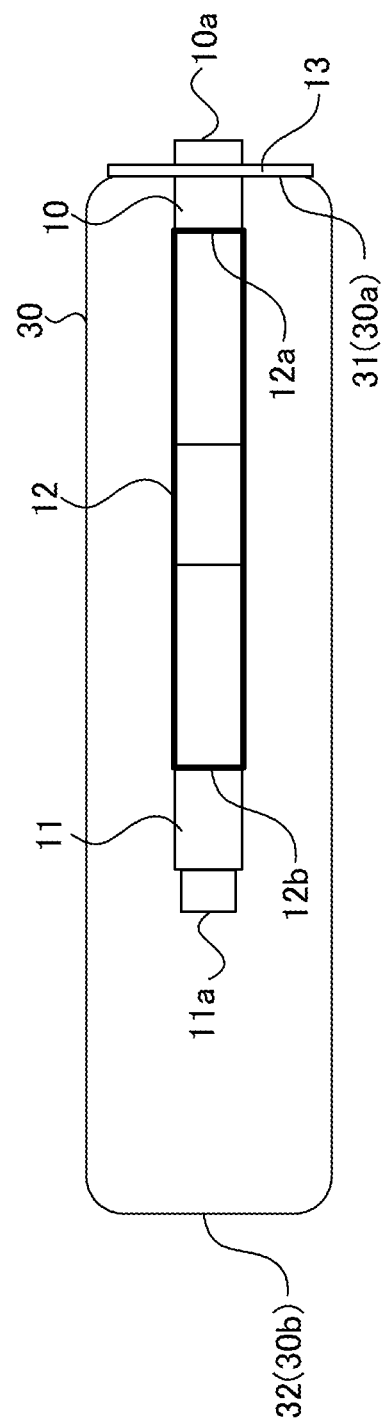
FIG. 1B is a schematic side view of the liquid supply apparatus according to the first embodiment of the present invention.
Figure 1C:
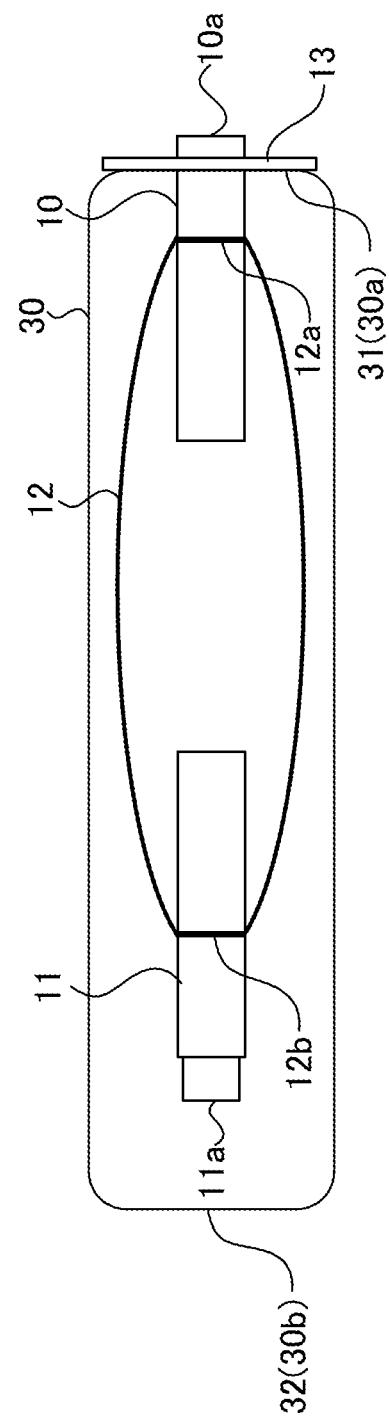
FIG. 1C is a schematic side view of the liquid supply apparatus according to the first embodiment of the present invention.

FIG. 1A to 1C each are a schematic side view of a liquid supply apparatus according to a first embodiment of the present invention. FIG. 1A illustrates the liquid supply apparatus excluding a casing. FIG. 1B illustrates the liquid supply apparatus including a casing. FIG. 1C illustrates the liquid supply apparatus including the casing in which a liquid is filled. The liquid supply apparatus according to the first embodiment can be used, for example, in outer space to supply water or liquid diet (organism rearing liquid, hereinafter referred to as water or the like) to organisms such as mice to be reared in outer space. In particular, the liquid supply apparatus according to the first embodiment can be mounted on a spacecraft for launch and/or recovery.

As illustrated in FIG. 1A, the liquid supply apparatus includes a first shaft 10 (first support member); a second shaft 11 (second support member) disposed in series (coaxially) with the first shaft 10; a balloon 12 having one end supported by the first shaft 10 and the other end supported by the second shaft 11; and a substantially cylindrical fixed plate 13 fixed to the first shaft 10.

The balloon 12 is configured so as to be able to hold therein water or the like to be supplied to organisms such as mice and discharge the water or the like therefrom. The first shaft 10 is a substantially cylindrical member. The first shaft 10 includes therein an outlet port 10a for letting out the water or the like held in the balloon 12. The outlet port 10a extends from one end of the first shaft 10 to the other end thereof. The second shaft 11 is a substantially cylindrical member. The second shaft 11 includes therein a filling port 11a for filling water or the like into the balloon 12. The filling port 11a extends from one end of the second shaft 11 to the other end thereof. The filling port 11a is configured to be opened and closed by an unillustrated lid. The outlet port 10a connects to an unillustrated pipe or the like.

The balloon 12 is a substantially cylindrical elastic member. The material of the balloon 12 is not particularly limited, but from the viewpoint of biocompatibility, for example, silicone rubber or the like is preferable. The balloon 12 is configured to be able to hold, for example, approximately 250 mL of water or the like.

The balloon 12 includes an outlet hole 12a provided on one end thereof. The balloon 12 is in close contact with the outer periphery of the first shaft 10 via the outlet hole 12a. Thus, the outlet port 10a of the first shaft 10 is in fluid communication with the outlet hole 12a of the balloon 12, and the inner space of the balloon 12 communicates with the outer space via the outlet port 10a. In addition, the balloon 12 includes a filling hole 12b provided on the other end thereof. The balloon 12 is in sealingly contact with the outer periphery of the second shaft 11 via the filling hole 12b. Thus, the filling port 11a of the second shaft 11 is in fluid communication with the filling hole 12b of the balloon 12, and the inner space of the balloon 12 communicates with the outer space via the filling port 11a.

As illustrated in FIG. 1B, the liquid supply apparatus according to the first embodiment further includes a tubular casing 30 having a constant longitudinal length. Note that as used herein, the term "tubular" is not limited to a cylindrical shape but includes a rectangular tubular shape having a polygonal cross section. The casing 30 includes a substantially circular first opening 30a provided in a first end portion 31; and a substantially circular second opening 30b provided in a second end portion 32 opposite to the first end portion 31. The casing 30 includes therein the first shaft 10, the balloon 12, and the second shaft 11. The fixed plate 13 is fixed to the first end portion 31 of the casing 30 so as to close the first opening 30a of the casing 30. Therefore, one end portion of the first shaft 10 is positioned outside the casing 30. The balloon 12 or the second shaft 11 does not contact the casing 30 and is not fixed thereto.

When the fixed plate 13 is fixed to the first end portion 31, first, the first shaft 10 including the fixed plate 13, the balloon 12, and the second shaft 11 are inserted into the casing 30 through the first opening 30a. Then, the fixed plate 13 is fixed to the first end portion 31 of the casing 30 from outside the casing 30 so that the fixed plate 13 closes the first opening 30a.

In order to cause the balloon 12 of the liquid supply apparatus to hold water or the like, an unillustrated liquid source is connected to the filling port 11a of the second shaft 11 to supply water or the like into the balloon 12. Note that an unillustrated pipe or the like connected to the outlet port 10a of the first shaft 10 is closed by a valve or the like to prevent water or the like supplied into the balloon 12 from continuing to flow out of the outlet port 10a. As water or the like is supplied into the balloon 12, the balloon 12 inflates in the axial direction of the first shaft 10 and in the radial direction of the first shaft 10 as illustrated in FIG. 1C. Note that if the balloon 12 contacts the inner side surface of the casing 30 before the balloon 12 is completely inflated by being filled with a predetermined amount of water or the like, the contact may prevent the inflation. In light of this, the balloon 12 can be inflated so as to be oriented in a predetermined direction by preliminarily inflating the balloon 12 into a desired shape using a gas such as air and nitrogen. More specifically, the balloon 12 can be more easily inflated in the axial direction of the first shaft 10 than in the radial direction thereof. Thus, when the balloon 12 is completely inflated by holding water or the like, the axial expansion coefficient of the first shaft 10 of the balloon 12 is greater than the radial expansion coefficient of the first shaft 10 of the balloon 12. This configuration can suppress the balloon 12 from contacting the inner surface of the casing 30 before being completely inflated.

As illustrated in FIG. 1C, when the balloon 12 holds water or the like, the second shaft 11 moves in an (axial) direction away from the first shaft 10. When the balloon 12 is completely inflated by holding water or the like, one end supported by the first shaft 10 of the balloon 12 and the other end supported by the second shaft 11 are positioned so as to be contained within the casing 30. More specifically, as illustrated in FIG. 1C, in a side view of the liquid supply apparatus, the balloon 12 is inflated so as not to protrude from the casing 30. This configuration ensures that the balloon 12 is always located within the casing 30, can prevent the balloon 12 from contacting external objects, and can prevent the balloon 12 from being damaged.

As illustrated in FIG. 1C, in a state where the balloon 12 is completely inflated by holding water or the like, the filling port 11a of the second shaft 11 is sealed by an unillustrated lid or the like, whereby the water or the like is held by the balloon 12 without leaking from the balloon 12.

In order to supply water or the like to organisms such as mice using the liquid supply apparatus illustrated in FIG. 1C, a valve of an unillustrated pipe or the like connected to the first shaft 10 is opened. Then, the contraction force of the balloon 12 causes the water or the like inside the balloon 12 to be pushed out from the outlet port 10a into the pipe, whereby the water or the like can be automatically supplied to organisms such as mice.

As described above, the liquid supply apparatus according to the first embodiment can stably supply water or the like by the contraction force of the balloon 12, and thus can eliminate the need for a power supply for supplying water or the like. In addition, the liquid supply apparatus according to the first embodiment eliminates the need for a power supply and thus can relatively reduce weight and foot print more than the conventional liquid supply apparatus needing an electric power supply or the like.

In addition, the liquid supply apparatus according to the first embodiment includes a casing 30 having a constant longitudinal length, and the balloon 12 is disposed in the casing 30. When the balloon 12 holds liquid, one end and the other end of the balloon are positioned in the casing 30. This configuration ensures that the balloon 12 is always located within the casing 30, can prevent the balloon 12 from contacting external objects, and can prevent the balloon 12 from being damaged.

In the liquid supply apparatus according to the first embodiment, the first shaft 10 is fixed to one end of the casing 30. When the balloon 12 holds water or the like, the axial expansion coefficient of the first shaft 10 of the balloon 12 is greater than the radial expansion coefficient of the first shaft 10 of the balloon 12. This configuration can suppress the balloon 12 from contacting the inner surface of the casing 30 before being completely inflated.

In the liquid supply apparatus according to the first embodiment, the first shaft 10 includes the outlet port 10a and the second shaft 11 includes the filling port 11a. Thus, even if the outlet port 10a connects to an unillustrated pipe or the like, water or the like can be filled into the balloon 12 through the filling port 11a. Note that in the present embodiment, the filling port 11a for filling water or the like is provided separately from the outlet port 10a for letting out water or the like, but another embodiment may be configured so as to fill water or the like through the outlet port 10a. In this case, in a state where the filling port 11a is closed, a liquid source is connected to the outlet port 10a to fill water or the like thereinto, and then a pipe or the like may be connected to the outlet port 10a.

The liquid supply apparatus according to the first embodiment can be used not only in outer space (zero gravity environment, microgravity environment) but also on the ground. In the case of an automatic liquid supply apparatus using gravity, a tank must be positioned higher than a supply port (outlet port) for water or the like. In contrast to this, the liquid supply apparatus according to the first embodiment is advantageous in that the positional relationship between the outlet port 10a and the balloon 12 is not limited to this position. In addition, the liquid supply apparatus according to the first embodiment can reduce the capacity of the balloon 12 (approximately 5 to 20 mL) to be used in conjunction with an orifice, thereby allowing continuous subcutaneous administration of drugs to a small animal. The liquid supply apparatus according to the first embodiment allows continuous administration of drugs, for example, at a flow rate of at least 0.5 mL/hr.

Second Embodiment

Figure 2A:
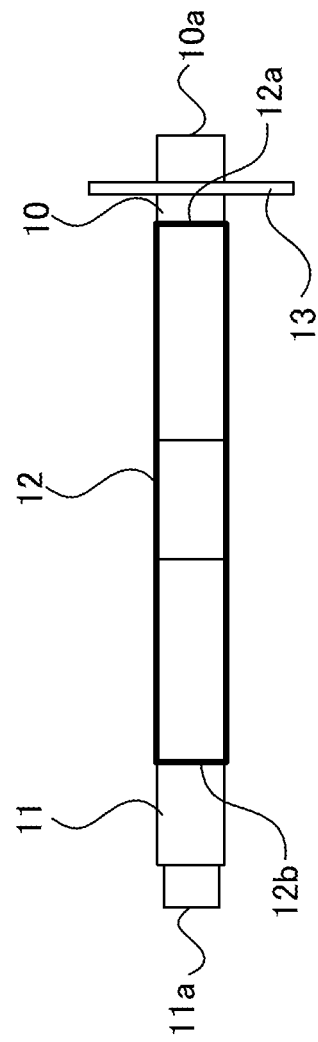
FIG. 2A is a schematic side view of a liquid supply apparatus according to a second embodiment of the present invention.
Figure 2B:
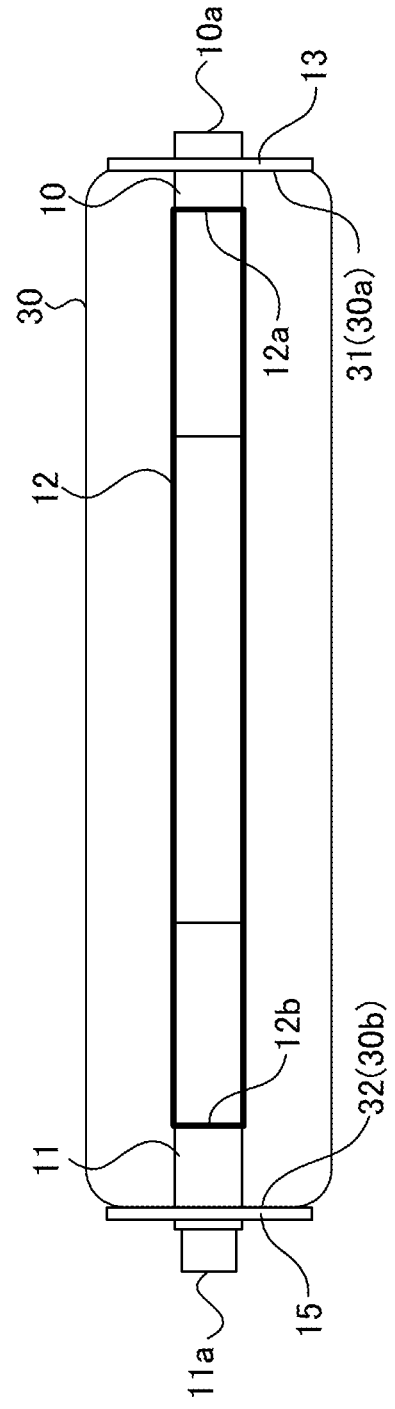
FIG. 2B is a schematic side view of the liquid supply apparatus according to the second embodiment of the present invention.

FIGS. 2A to 2C each are a schematic side view of a liquid supply apparatus according to a second embodiment of the present invention. FIG. 2A illustrates the liquid supply apparatus excluding a casing. FIG. 2B illustrates the liquid supply apparatus including a casing. FIG. 2C illustrates the liquid supply apparatus including the casing in which a liquid is filled. The liquid supply apparatus according to the second embodiment can be used, for example, in outer space to supply water or the like for rearing organisms such as mice to be reared in outer space, in the same manner as the liquid supply apparatus according to the first embodiment. In particular, the liquid supply apparatus according to the second embodiment can be mounted on a spacecraft on orbit.

The liquid supply apparatus according to the second embodiment differs from the liquid supply apparatus according to the first embodiment mainly in that the second shaft 11 is fixed to the casing 30. In the drawings described below, the same reference numerals or characters are assigned to the components same as or similar to those of the liquid supply apparatus according to the first embodiment, and the duplicate description is omitted.

As illustrated in FIG. 2A, the liquid supply apparatus excluding the casing 30 according to the second embodiment has the same configuration as the liquid supply apparatus excluding the casing 30 according to the first embodiment illustrated in FIG. 1A.

As illustrated in FIG. 2B, the second shaft 11 includes a substantially cylindrical fixed plate 15. The casing 30 includes therein the first shaft 10, the balloon 12, and the second shaft 11. The balloon 12 of the liquid supply apparatus according to the second embodiment is configured so as to be able to hold, for example, approximately 70 mL of water or the like. The fixed plate 13 is fixed to the first end portion 31 of the casing 30 so as to close the first opening 30a of the casing 30. Therefore, one end portion of the first shaft 10 is positioned outside the casing 30. Likewise, the fixed plate 15 is fixed to the second end portion 32 of the casing 30 so as to close the second opening 30b of the casing 30. Thus, one end portion of the second shaft 11 is positioned outside the casing 30.

When the fixed plate 13 and the fixed plate 15 are fixed to the first end portion 31 and the second end portion 32 respectively, first, the first shaft 10 including the fixed plate 13, the balloon 12, and the second shaft 11 are inserted into the casing 30 through the first opening 30a. Then, the fixed plate 13 is fixed to the first end portion 31 from outside the casing 30.

In a state in which the fixed plate 13 is fixed to the first end portion 31, the second shaft 11 is pulled toward the second end portion 32 (a tensile stress is applied) to stretch the balloon 12. In a state in which the balloon 12 is stretched to a position (position illustrated in FIG. 2C) where one end portion of the second shaft 11 protrudes from the casing 30, the fixed plate 15 is attached to the second shaft 11. At this time, the balloon 12 is preferably stretched to have a length of approximately 1.5 times or more in the axial direction of the first shaft 10 than that in a state (state illustrated in FIG. 2A) where no tensile stress is applied. Finally, the fixed plate 15 is fixed to the second end portion 32 from outside the casing 30. Thus, the balloon 12 is fixed to the first shaft 10 and the second shaft 11 in a state where a tensile stress is applied.

As illustrated in FIG. 2C, in order to allow the balloon 12 of the liquid supply apparatus to hold water or the like, an unillustrated liquid source is connected to the filling port 11a of the second shaft 11 to supply water or the like into the balloon 12. Note that an unillustrated pipe or the like connected to the outlet port 10a of the first shaft 10 is closed by a valve or the like to prevent water or the like supplied into the balloon 12 from continuing to flow out of the outlet port 10a.

As described above, the first shaft 10 and the second shaft 11 are fixed to the first end portion 31 and the second end portion 32 of the casing 30 by the fixed plate 13 and the fixed plate 15 respectively in a state where a tensile stress is applied to the balloon 12. When the thus configured balloon 12 is filled with water or the like, the balloon 12 can be suppressed from stretching in the axial direction of the first shaft 10 and the balloon 12 can be inflated in the radial direction of the first shaft 10. This configuration can suppress the balloon 12 from contacting the inner surface of the casing 30 before being completely inflated and can prevent inflation failure due to contacting of the balloon 12 with the inner surface of the casing 30.

As illustrated in FIG. 2C, in a state where the balloon 12 is completely inflated by holding water or the like, the filling port 11a of the second shaft 11 is sealed by an unillustrated lid or the like, whereby the water or the like is held by the balloon 12 without leaking from the balloon 12.

In order to supply water or the like to organisms such as mice using the liquid supply apparatus illustrated in FIG. 2C, a valve of an unillustrated pipe or the like connected to the first shaft 10 is opened. Then, the contraction force of the balloon 12 causes the water or the like inside the balloon 12 to be pushed out from the outlet port 10a into the pipe, whereby the water or the like can be automatically supplied to organisms such as mice.

As described above, the liquid supply apparatus according to the second embodiment can stably supply water or the like by the contraction force of the balloon 12, and thus can eliminate the need for a power supply for supplying water or the like. In addition, the liquid supply apparatus according to the second embodiment eliminates the need for a power supply and thus can relatively reduce weight and foot print more than the conventional liquid supply apparatus needing an electric power supply or the like.

In addition, the liquid supply apparatus according to the second embodiment includes a casing 30 having a constant longitudinal length, and the balloon 12 is disposed in the casing 30. When the balloon 12 holds liquid, one end and the other end of the balloon are positioned in the casing 30. This configuration ensures that the balloon 12 is always located within the casing 30, can prevent the balloon 12 from contacting external objects, and can prevent the balloon 12 from being damaged.

In the liquid supply apparatus according to the second embodiment, the first shaft 10 is fixed to the first end portion 31 of the casing 30 and the second shaft 11 is fixed to the second end portion 32. In addition, the balloon 12 is supported by the first shaft 10 and the second shaft 11 in a state where a tensile stress is applied. In other words, because of a constant distance between the first shaft 10 and the second shaft 11, the balloon 12 has a constant axial width along the first shaft 10. When the balloon 12 is filled with water or the like, the balloon 12 can be suppressed from inflating in the axial direction of the first shaft 10 and the balloon 12 inflates in the radial direction of the first shaft 10, and thus the inflation shape of the balloon 12 can be controlled. Therefore, the balloon 12 can be inflated into a desired shape inside the casing 30, and the balloon 12 can hold more water or the like in the limited space inside the casing 30.

In addition, the balloon 12 is supported by the first shaft 10 and the second shaft 11 in a state where a tensile stress is applied to have a length of 1.5 times or more in the axial direction of the first shaft 10 than that in a state where no tensile stress is applied. This configuration can more reliably suppress the balloon 12 from inflating in the axial direction of the first shaft 10 and can inflate the balloon 12 in the radial direction of the first shaft 10.

In liquid supply apparatus according to the second embodiment, the first shaft 10 includes the outlet port 10a and the second shaft 11 includes the filling port 11a. Thus, even if the outlet port 10a connects to an unillustrated pipe or the like, water or the like can be filled into the balloon 12 through the filling port 11a. Note that in the present embodiment, the filling port 11a for filling water or the like is provided separately from the outlet port 10a for letting out water or the like, but another embodiment may be configured so as to fill water or the like through the outlet port 10a. In this case, in a state where the filling port 11a is closed, a liquid source is connected to the outlet port 10a to fill water or the like thereinto, and then a pipe or the like for letting out water or the like may be connected to the outlet port 10a.

The liquid supply apparatus according to the second embodiment can be used not only in outer space (zero gravity environment, microgravity environment) but also on the ground. In the case of an automatic liquid supply apparatus using gravity, a tank must be positioned higher than a supply port (outlet port) for water or the like. In contrast to this, the liquid supply apparatus according to the second embodiment is advantageous in that the positional relationship between the outlet port 10a and the balloon 12 is not limited to this position. In addition, the liquid supply apparatus according to the second embodiment can reduce the capacity of the balloon 12 (approximately 5 to 20 mL) to be used in conjunction with an orifice, thereby allowing continuous subcutaneous administration of drugs to a small animal. The liquid supply apparatus according to the second embodiment allows continuous administration of drugs, for example, at a flow rate of at least 0.5 mL/hr.

The above described liquid supply apparatus according to the first embodiment can also be mounted on a spacecraft on orbit. Likewise, the liquid supply apparatus according to the second embodiment can also be mounted on a spacecraft for launch and/or recovery.

Hereinbefore, the embodiments of the present invention have been described, but the present invention is not limited to the above embodiments, and various modifications can be made within the scope of the claims and within the scope of the technical ideas described in the specification and the drawings. Note that any shape and material not directly described in the specification and the drawings are within the scope of the technical ideas of the present invention as long as they exhibit the operation and effects of the present invention.

REFERENCE SIGNS LIST 10 first shaft
10a outlet port 11 second shaft
11a filling port
12 balloon
30 casing

What is claimed is:

1. A liquid supply apparatus comprising:
a first support member;
a second support member;
a balloon having a first end supported by the first support member and a second end supported by the second support member; and
a casing having a constant longitudinal length, wherein;
the first support member is fixed to one end of the casing;
the second support member is fixed to another end of the casing;
the balloon is supposed by the first support member and the second support member in a state where a tensile stress is applied;
the second support member includes a filling port for filling the liquid into the balloon;
the balloon is disposed in the casing and is configured so as to be able to hold therein a liquid to be supplied and discharge the held liquid;
the balloon is configured to have a completely inflated state in which the balloon is completely filled with the liquid without contacting an inner surface of the casing, and in which the filling port is sealed; and
the first end and the second end of the balloon are positioned in the casing in the completely filled state.

2. The liquid supply apparatus according to claim 1, wherein
the balloon is supported by the first support member and the second support member in a state where a tensile stress is applied so as to have a length of 1.5 times or more in an axial direction of the first support member than that in a state where no tensile stress is applied.

3. The liquid supply apparatus according to claim 1, wherein when the balloon holds the liquid, an axial expansion coefficient of the first support member of the balloon is greater than a radial expansion coefficient of the first support member of the balloon.

4. The liquid supply apparatus according to claim 1, wherein
the first support member includes an outlet port for letting out the liquid held in the balloon; and
the balloon includes an outlet hole in fluid communication with the outlet port of the first support member and a filling hole in fluid communication with the filling port of the second support member.

5. The liquid supply apparatus according to claim 1, wherein
the balloon is made of silicone rubber.

6. The liquid supply apparatus according to claim 1, wherein
the liquid is a liquid for rearing organisms.

7. The liquid supply apparatus according to claim 1, wherein the liquid supply apparatus is used in outer space.

8. The liquid supply apparatus according to claim 1, further comprising;
the liquid held in the balloon, wherein;
the balloon is configured not to contact the inner surface of the casing when the balloon holds the liquid therein.

9. The liquid supply apparatus according to claim 1, wherein:
the balloon is configured to hold a predetermined amount of the liquid in the completely inflated state.

10. The liquid supply apparatus according to claim 1, wherein:
the balloon is configured to have a maximum diameter in the completely inflated state that is less than a diameter of the inner surface of the casing.

* * * * *